(12) United States Patent
Breviglieri et al.

(10) Patent No.: US 6,538,142 B1
(45) Date of Patent: Mar. 25, 2003

(54) PROCESS FOR THE PREPARATION OF METAXALONE

(75) Inventors: Gabriele Breviglieri, Treviglio (IT); Sergio Contrini, Treviglio (IT); Giacomo Bruno, Treviglio (IT); Cinzia Assanelli, Treviglio (IT)

(73) Assignee: Farchemia S.r.l., Treviglio (IT)

( * ) Notice: Subject to any disclaimer, the term of this patent is extended or adjusted under 35 U.S.C. 154(b) by 0 days.

(21) Appl. No.: 10/124,474

(22) Filed: Apr. 18, 2002

(51) Int. Cl.$^7$ .................. C07D 263/04; C07D 263/16; C07D 263/20; C07D 263/38
(52) U.S. Cl. .................. 548/229; 548/225; 564/336; 564/348; 568/655; 549/555; 549/563; 560/179
(58) Field of Search .................. 548/229, 225; 564/336, 348; 568/655; 549/555, 563; 560/179

(56) References Cited
FOREIGN PATENT DOCUMENTS

FR          1487641      *   7/1967

OTHER PUBLICATIONS

Takahashi et al, J. Am. Chem. Soc. 1990, 112, 5876–5878.*
Vigroux et al, J. Med. Chem. 1995, 38, 3983–3994.*

* cited by examiner

*Primary Examiner*—Ceila Chang
*Assistant Examiner*—Rei-Tsang Shiao
(74) *Attorney, Agent, or Firm*—Young & Thompson

(57) ABSTRACT

A process for the preparation of 5-(3,5-dimethylphenoxymethyl)-2-oxazolidinone, which includes:
   a) reacting 3,5-dimethylphonel with epichlorohydrin to obtain a mixture of 1-(3,5-dimethylphenoxy)2,3-epoxy propane (1) and 1-(3,5-dimethylphenoxy)-3-chloro-2-propanol (2);
   b) reacting the mixture of (1) and (2) obtained from step (a) with benzylamine to obtain a first compound;
   c) reducing the first compound with hydrogen in presence of ammonia, to obtain a second compound; and
   d) reacting the second compound with dimethylcarbonate in the presence of a strong base to obtain 5-(3,5-dimethlphenoxymethyl)-2-oxazolidinone.

7 Claims, No Drawings

PROCESS FOR THE PREPARATION OF METAXALONE

The present invention relates to a process for the preparation of metaxalone or 5-(3,5-dimethylphenoxymethyl)-2-oxazolidinone.

The latter is a known muscle relaxing agent of the group of 5-aryloxymethyl-oxazolidones, and was initially described in U.S. Pat. No. 3,062,827. In this patent, different routes of synthesis of metaxalone are proposed. For example, the compound is prepared by reacting 3-(3',5'-dimethylphenoxy)-1,2-propanediol and urea at a temperature of 195–200° C. Alternatively, the selected 3-phenoxy-1-chloro-2-propanol may be reacted with urea instead of the phenoxy-1,2-propanediol under the same conditions. The 5-(3',5'-dialkylphenoxymethyl)-2-oxazolidones may also be prepared by reacting a selected 3-phenoxy-2-hydroxy-1-propylcarbamate and urea in equimolar quantities and at elevated temperatures.

The synthesis reported in GB1104773 comprises the reaction of 3,5-dimethyl-phenol with triglycidyl isocyanurate in an organic solvent using a phenol/isocyanurate molar ratio of about 1:3.

Object of this invention is a process for the preparation of metaxalone, which comprises:

a) reaction of 3,5-dimethylphenol with epichlorohydrin to obtain a mixture of 1-(3,5-dimethylphenoxy)2,3-epoxy propane (1) and 1-(3,5-dimethylphenoxy)-3-chloro-2-propanol (2):

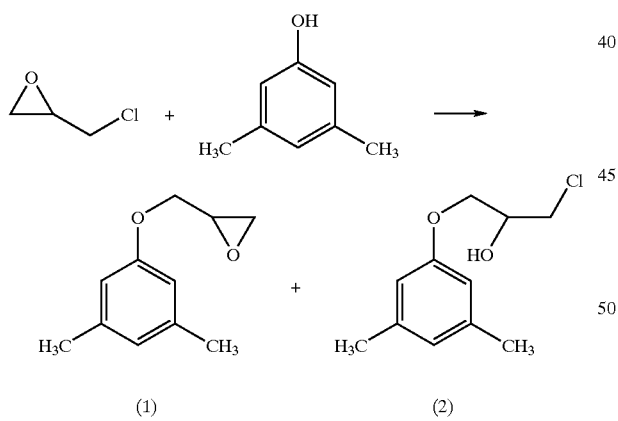

b) reaction of the mixture of (1) and (2) obtained from step (a) with benzylamine to give (3):

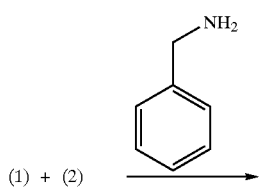

(1) + (2) →

-continued

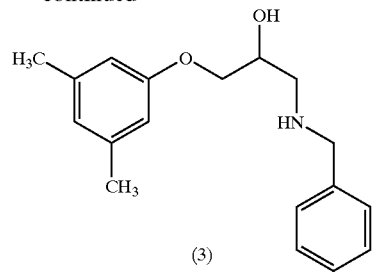

c) reduction of (3) with hydrogen in presence of ammonia, to give (4):

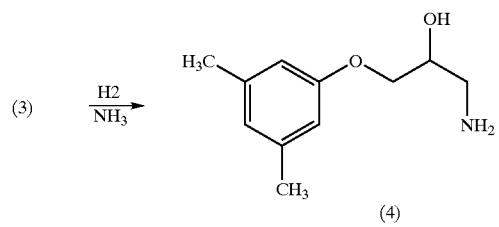

d) reaction of (4) with dimethylcarbonate in the presence of a strong base to give 5-(3,5-dimethylphenoxymethyl)-2-oxazolidinone (5):

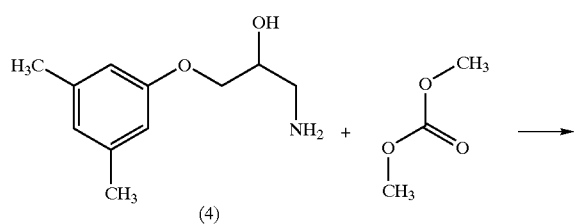

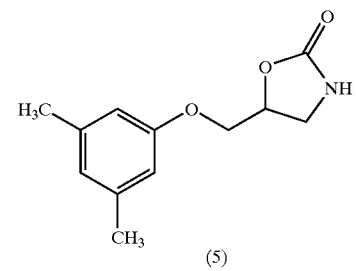

In step (a) the mixture of reactants is usually heated at reflux temperature in the presence of a quaternary ammonium salt for a period sufficient to have complete conversion into (1) and (2). Once the reaction is completed, the excess epichlorohydrin as well as any 1,3-dichloropropanol by-product are distilled off.

In step (b) a mixture of (1) and (2) is added to an excess of benzylamine, heating to a temperature of 130°–135° C. At the end a strong base is added to free benzylamine which is distilled off.

The reduction step (c) can be carried out with gaseous hydrogen in the presence of a Pd/C catalyst and ammonia. Once the reaction (which is monitored by HPLC) is terminated, the catalyst is filtered off, the pH is adjusted at 10–13 units and the solution is extracted with organic solvents. The organic layers are collected and extracted with an acidic aqueous solution at pH 4, the organic phase is discarded. Solvent is added to the aqueous phase and the mixture is made alkaline by addition of sodium hydroxide. The aqueous layer is separated and product (4) is recovered by distilling off the solvent.

In step (d) product (4) is reacted with dimethylcarbonate in the presence of a metal alkoxide, preferably sodium methoxide, at reflux temperature. The excess dimethylcarbonate is distilled off and product (5) is taken up with an organic solvent and washed with aqueous hydrogen chloride and sodium hydroxide. The organic solution is dried and the product crystallizes by cooling.

The following example illustrates the invention in greater details.

EXAMPLE

Synthesis of Metaxalone

| First step | |
|---|---|
| 3,5-xilenol | 40 g |
| epichlorohydrin | 200 g (fresh + recycled) |
| Tetrabutylammonium bromide | 1 g |

All reactants are loaded in the reaction vessel and the mixture is warmed at reflux (130° C.) for 3 hours. The reflux temperature gradually decreases from 130° to 125° C.

(The end of reaction is determined by HPLC). After this time a vigreaux column is installed on the flask. Epichlorohydrin excess is removed by distillation under a vacuum of 45 mm/Hg till the internal temperature of 100° C. is reached. The recovered epichlorohydrin (140 g) can be recycled. A vacuum of 10 mm/Hg is applied and the mixture is distilled till the internal temperature of 120° C. is reached; the distilled product is 1,3-dichloropropanol that is discarded. The residue (65 g) is a mixture of 1-(3,5-dimethylphenoxy)-2,3-epoxy-propane and 1-(3,5-dimethylphenoxy)-3-chloro-2-propanol, which is used as such in the following step.

| Second step | |
|---|---|
| Residue from step 1 | 65 g |
| benzylamine | 170 g |

The residue of previous step is slowly dropped into benzylamine which was previously heated to 80° C. (In this conditions only the epoxyde (1) reacts).

The mixture is heated to 130°–135° C. for 8 hours. At this temperature also the chlorohydrin (2) reacts (the end of reaction is determined by HPLC).

The mixture is cooled at 40° C. and a mixture of 20 ml NaOH 30% (w/w) and 10 ml water is added in 15'. (benzylamine hydrochloride, formed during the reaction, gives the free base).

Stirring is stopped and the lower aqueous phase is discarded.

The excess of benzylamine is distilled, first under 40–50 mm/Hg and then under 2–3 mm/Hg till the internal temperature of 130°–140° C. is reached. The recovered benzylamine (110–120 g) can be recycled. The residue (about 130 g) is used in the following step.

Third Step

The residue of previous step is heated to 50° C. and 100 ml of methanol are added. The solution is cooled at 20° C. and transferred into an autoclave.

100 ml of 30% (w/w) ammonia and 2.5 g of 10% Pd/c are added.

5 bar of hydrogen are introduced.

The mixture is warmed at 130° C. (the pressure reaches 12–13 atm) for 8 hours. Hydrogen is added, if necessary, to maintain ad least 10 atm. The end of reaction is determined by HPLC.

The solution is cooled ad 20° C. and the catalyst is filtered off.

The solution is distilled at atmospheric pressure until an internal temperature of 90° C. is reached. The pH is adjusted to 12 with 30% NaOH, and then 100 ml toluene are added. After stirring 15' the aqueous layer is separated and extracted again with 50 ml of toluene.

100 ml of water are added to the organic phase. Acetic acid is added to acidify at pH 4.

The organic phase is separated and discarded. Charcoal is added to the aqueous phase which is then filtered on inert support.

100 ml of toluene are added to the filtered aqueous solution.

NaOH 30% is added to reach pH 12.

The aqueous layer is separated and discarded. The organic phase is distilled under vacuum (50 mm/Hg) till an internal temperature of 90° C. is reached. The residue (about 54 g) is used in the following step.

Final Step 250 ml of dimethyl carbonate and 2.5 ml of sodium methoxyde 30% solution in methanol are added to the residue of previous step. The mixture is refluxed for 3 hours. (HPLC control). If the reaction is not complete, 1.5 ml of sodium methoxyde are added and the mixture is refluxed for additional 2 hours (HPLC control).

When the reaction is completed the excess of dimethyl carbonate is distilled at atmospheric pressure till an internal temperature of 100° C. is reached (210 ml of dimethyl carbonate are recovered).

150 ml of toluene and 30 ml of water are added to the residue; HCl 35% is added to reach pH 0.5. The aqueous layer is separated at 60° C. and discarded. The organic solution is added with 30 ml of water and the pH is adjusted to 7.0 with NaOH 30%. The aqueous phase is separated and discarded at 60° C. The organic phase is dried by distillation with a Dean-Stark apparatus. The solution is treated with charcoal, heated at reflux and then filtered, with heat, on inert support.

The filter is washed with hot toluene.

The solution is cooled to 20° C. and then to 0° C. for 3 hours. The product is filtered and washed with 40 ml of cold toluene. The product is dried under vacuum at 60° C.

40–42 g are obtained.

The product is crystallized by dissolving it in 4 volumes of toluene at reflux.

Charcoal is added and the hot solution is filtered on an inert support. The filter is washed with hot toluene.

The solution is cooled to 20° C. and then to 0° C. for 3 hours. The product is filtered and washed with 40 ml of cold toluene. 39–40 g of pure metaxalone are obtained.

What is claimed is:

1. A process for the preparation of 5-(3,5-dimethylphenoxymethyl)-2-oxazolidinone, which comprises:

a) reaction of 3,5-dimethylphenol with epichlorohydrin to obtain a mixture of 1-(3,5-dimethylphenoxy)2,3-epoxy propane (1) and 1-(3,5-dimethylphenoxy)-3-chloro-2-propanol (2):

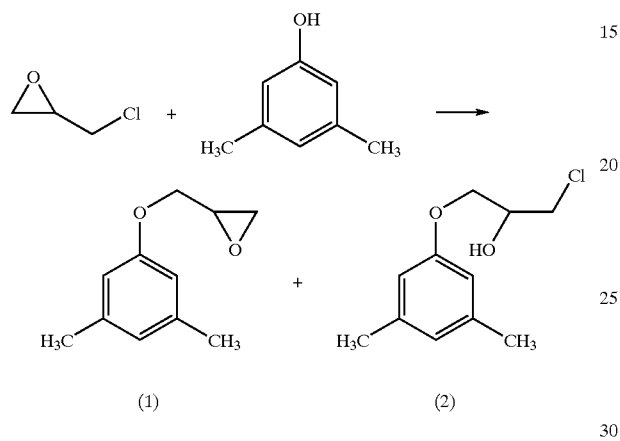

b) reaction of the mixture of (1) and (2) obtained from step (a) with benzylamine to give (3):

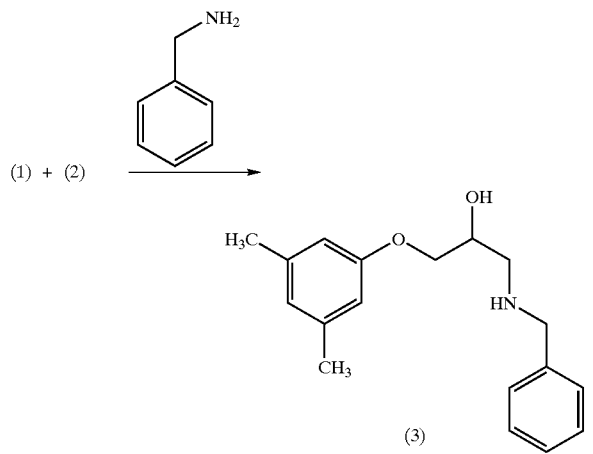

c) reduction of (3) with hydrogen in presence of ammonia, to give (4):

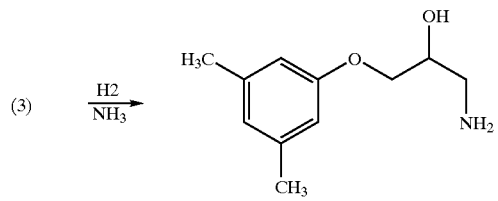

d) reaction of (4) with dimethylcarbonate in the presence of a strong base to give 5-(3,5-dimethylphenoxymethyl)-2-oxazolidinone (5):

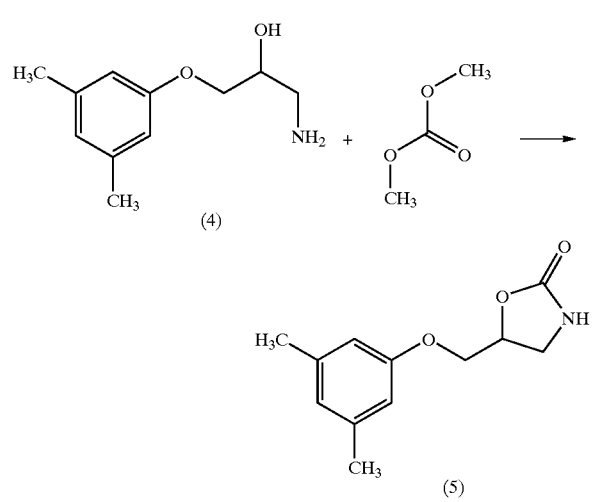

2. A process according to claim 1, wherein step (a) is carried out by heating a mixture of epichlorohydrin and 3,5-dimethylphenol at reflux temperature in the presence of a quaternary ammonium salt.

3. A process according to claim 1, wherein step (b) is carried out by adding the product of step (a) to a benzylamine excess and heating to a temperature of 130–135° C.

4. A process according to claim 1, wherein step (c) is carried out using gaseous hydrogen in the presence of a Pd/C catalyst and ammonia.

5. A process according to claim 1, wherein product (4) is reacted in step (d) with dimethylcarbonate in the presence of a metal alkoxide at reflux temperature.

6. A process according to claim 5, wherein said metal alkoxide is sodium methoxide.

7. A process according to claim 1, further comprising the crystallization of product (5) in toluene.

* * * * *